United States Patent [19]
De Liotta et al.

[11] Patent Number: 4,655,772
[45] Date of Patent: Apr. 7, 1987

[54] CARDIAC VALVULAR PROSTHESIS

[76] Inventors: Holga E. T. De Liotta; Domingo S. Liotta, both of 3 de Febrero 2025, Buenos Aires, Argentina

[21] Appl. No.: 738,222

[22] Filed: May 28, 1985

[30] Foreign Application Priority Data

Sep. 19, 1984 [AR] Argentina .............................. 298006

[51] Int. Cl.$^4$ ............................................. A61F 2/24
[52] U.S. Cl. ...................................................... 623/2
[58] Field of Search ........................................... 623/2

[56] References Cited

U.S. PATENT DOCUMENTS

| | | | |
|---|---|---|---|
| Re. 30,507 | 2/1981 | Kaster | 623/2 |
| 3,825,956 | 7/1974 | Child | 623/2 |
| 3,825,957 | 7/1974 | Kaster | 623/2 |
| 3,959,827 | 6/1976 | Kaster | 623/2 |
| 4,021,863 | 5/1977 | Woien | 623/2 |
| 4,197,593 | 4/1980 | Kaster et al. | 623/2 |
| 4,319,364 | 3/1982 | Kaster | 623/2 |
| 4,363,142 | 12/1982 | Meyer | 623/2 |
| 4,373,216 | 2/1983 | Klawitter | 623/2 |
| 4,416,029 | 11/1983 | Kaster | 623/2 |
| 4,535,484 | 8/1985 | Marconi | 623/2 |

Primary Examiner—Richard J. Apley
Assistant Examiner—Alan W. Cannon
Attorney, Agent, or Firm—Collard, Roe & Galgano

[57] ABSTRACT

A mechanical-type, bivalve cardiac valvular prosthesis including a support ring defining a central opening passing therethrough and a pair of relatively rigid leaflets, each having a diametrical straight edge and a curved edge, disposed generally within the central opening. The pair of leaflets are pivotably supported on the support ring to permit the leaflets to move between an open position, in which the leaflets are disposed generally parallel to the axis of the support ring so that said central opening remains substantially cleared, and a closed position, in which the opening is substantially blocked by the leaflets. The leaflets are each pivotably supported by a pair of pivot supports rigidly joined at one end to the inner surface of the support ring and each having an opposite, generally hook-shaped, free end on which the leaflet associated therewith is mounted in a free floating manner so that the leaflets are pivotable about a virtual axis parallel to the diametrical straight edges thereof and passing through the zone of the center of curvature of the hook-shaped ends of the pivot supports.

13 Claims, 5 Drawing Figures

CARDIAC VALVULAR PROSTHESIS

The present invention relates to a cardiac valvular prosthesis. More particularly, it relates to such a prosthesis of the bivalve mechanical type.

It is known in the art that, for replacing irreparably damaged cardiac valves, prostheses of several types can be used. One type is a bivalve mechanical valve which includes: (a) a valve body stent, support or valvular seat ring, of generally annular shape, constituting the fixed or static element which is joined, preferably with a suture, to the zone surrounding the valve to be replaced; (b) a movable valve element alternately allowing and interrupting the passage of blood flow according to the respective cardiac cycle in its periods of systole and diastole; and (c) a connecting element, such as articulations or joints, connecting the movable valve element with the support ring. The articulation or joint between the fixed supporting element and the movable element is of utmost importance in the design of a cardiac valvular prosthesis.

A number of different devices of the aforementioned type has been developed with varied results. Among those using mechanical valves, and including as a movable valve element a ball suitably retained within a wire cage or basket fixed to the ring, are, e.g. the Starr-Edwards and Smeloff-Cutter prostheses; those having a disc instead of a ball are, e.g. the Bjork-Shiley, Hall-Kaster, Omniscience, Wada and Beall prostheses; and with respect to bivalve mechanical prostheses, St. Jude Medical, Hemex and Duromedics, among others, may be noted.

These valves may also be distinguished based upon their mode of articulation, per se, as indicated below:

(a) remote articulation valves, of the cage type: e.g., Starr-Edwards, Beall, Smeloff-Cutter, (b) valves having the articulation in the fixed support ring; e.g., Omniscience (disc type), St. Jude Medical, Hemex and Duromedics (bivalve type), (c) valves having the articulation in the circular chord area of the support ring, e.g., Bjork-Shiley (disc type); and (d) valves having the articulation in the central area of the support ring; e.g. Hall-Kaster (disc type).

In hemodynamics there exists the following four well-known factors:

1. The well-known phenomenon that blood layers adjacent to the vessel endothelium or to the heart endocardium are barely displaced during normal circulation of the blood. It is known that this is due to an internal friction problem of the elements suspended by the blood during circulation. Under normal conditions, circulation occurs in concentric layers. The "central cylinder" of the blood column is that acquiring the greater velocity. This is referred to in circulatory physiology as "parabolic velocity profile during laminar flow".

2. Blood viscosity notably increases when flow velocity decreases. Upon contact with the endothelium or endocardium, the viscosity may increase up to ten times its normal value.

3. The decrease of velocity and increase of blood viscosity are key factors for local thrombosis.

4. Local thrombosis and subsequent thromboembolism is the most frequent complication after implantation of a mechanical valvular prosthesis in the heart notwithstanding the use of anticoagulant treatments.

Additionally, a well-known phenomenon in hemodynamics is that of the production of a turbulent flow when an obstacle is interposed in the central, maximum velocity zone of the blood flow; either in the center of blood vessels or in the center of the cardiac valve area.

In the aforementioned mechanical vales, some or all of the above factors are involved, especially with the presence of obstacles resulting in turbulences. Furthermore, the possibility of the formation of clots in the area of the articulation pins exists, as well as, in the case of articulated discs or semi-discoidal double valves in the supporting ring per se. The ideal design, therefore, would be one in which the mechanical valve, when in its open position, would allow for an ample central free zone and, additionally, would be free of articulated joints on all the inner surfaces of the support ring.

Hemex, Duromedics and St. Jude valves which are at present accepted by specialists, are very close to this ideal design; however, a drawback in their design is that, although they allow an ample central flow zone to expedite the free flow of blood, they include four articulations, with their respective pins, and limit stops located on the inner surface of the support ring; i.e., the articulation mechanism controlling the movement between the fixed and movable elements, is located in the zone of less velocity and greater viscosity of the blood, thereby running the risk of thrombosis formation and other consequences previously discussed.

Also close to ideal designs are free disc valves and those having a disc perforated in their center which have no pin articulations on the inner surface of the support ring. However, when placed in the opening position, they inhibit the blood flow precisely in central zones of maximum velocity, thereby causing the aforementioned turbulence risks which may provoke excessive hemolysis.

If, on the other hand, the valve is designed with an exaggerated opening, e.g., 70°-80°, the "stress" caused on the heart tissues by the shock produced during the valvular closure would be considerable.

Accordingly, it is an object of the present invention to solve the problems inherent in the prior art that have been discussed above, e.g., risks of thrombosis formation and excessive hemolysis, among others.

These objects, as well as others which will hereinafter become apparent, are accomplished in accordance with the present invention by providing two free swivelling and floating leaflets or valve elements in a bivalve mechanical type valvular prosthesis of the type including a rigid support ring surrounded by a conventional suture chord and support. As a valvular element, a pair of substantially flat leaflets (leaflets) are used movable between an open and closed position which, when in an opening position, are mutually parallel to the longitudinal axis of the assembly; the mutual separation of the leaflets in such opening position being, preferably, one third of the inner diameter of the support ring. The inventive valve is particularly characterized by the fact that there are no relative articulation members between the leaflets and the ring on the inner surface thereof; both leaflets (leaflets) are held by respective pairs of parallel pivot supports rigidly joined or otherwise fixed to the ring. The pivot supports are hook-shaped in their free ends which are directed toward the central area of the rigid ring cavity; the pivot supports loosely passing through respective orifices in the leaflets, the latter of which freely and independently swivel with respect to both transversal and parallel virtual axes passing through the interior of the hook-shaped ends of the pivot supports. Both leaflets, in their closing position, form angles of approximately 40° with respect to the plane defined by the cited virtual axes. In the opening position, the leaflets form angles of approximately 90° with respect to the same plane.

The leaflets each have a straight edge and an arcuate edge. In the closed position, the arcuate edge of each valve preferably makes no contact with the fixed support ring, except at the rim of the arcuate edge. This important feature allows this prosthesis to be desired as a "floating" prosthesis. This feature is further confirmed during the opening position in which the arcuate edge, as well as the straight edge of the leaflets, again makes no contact with the fixed support ring., i.e., remains "floating" inside the cavity of the fixed supporting ring. On the other hand, in the opening position, a greater central space for the passage of blood flow is provided.

Preferably, the two leaflets are formed by two substantially planar rigid elements, each having a generally semicircular shape. The leaflets are mounted so that they may swivel with respect to both virtual axes mutually parallel and separated to the extent required, which normally will be equal to a third of the internal diameter of the support ring. In the opening position, the planar elements are disposed parallel to one another and with respect to the axis of the supporting ring, thereby, providing a free passage between them which is notably greater than that provided by known valves.

The swivelling leaflets operate, as indicated, due to the novel mounting which is the most important feature of the invention. This mounting is carried out by means of four pivot supports, preferably in the form of wire elements, disposed as two pairs of parallel elements, in which the pivot supports of one pair are disposed opposite the pivot supports of the other pair. Each pivot support has the shape of a wire hook, one end of which is rigidly fixed to the support ring and the other end of which is hook shaped. In its curved or hook parts, the pivot supports loosely pass through corresponding orifices in the leaflets with the proviso that the hook shape should be such that each leaflets maintains a permanent connection to its respective pair of pivot supports or wire elements, without becoming disengaged therefrom, whatever its relative position may be.

Obviously, the four pivot supports or engagement wire elements, when fixed to the support ring, constitute discontinuities or interruptions of the inner surface of the ring which may conceivably serve as an obstacle just where the blood has its lower circulating velocity. However, there are presently available high strength materials, or, at least, sufficiently resistant material for suitably performing the aforesaid function with a relatively reduced or minimal cross section, thus rendering the incidence of the four pivot supports practically negligible as compared to that of known articulations; especially as compared to those devices with articulations located in the fixed support ring.

With the prosthesis of the present invention, in its position of total opening of the two leaflets, due to its arrangement and shape, three areas are attained inside the support ring which may be practically equivalent, namely: two side areas and a central area. However, the central area may be readily increased or decreased with respect to the side areas by modifying the position of the orifices through which the hook-shaped pivot supports holding the leaflets pass.

With this prosthesis, the final opening angle, naturally determined by the shape and arrangement of the pivot supports may be further fixed by adding two small stops per leaflets, each located at conveniently selected points on the inner surface of the support ring.

Further, the prosthesis of the invention, particularly when it is intended to replace a mitral valve, may optimally include an element in the form of a stem rigidly fixed to at least one of the leaflets in order to aid in the simultaneous opening movement of the other leaflets and vice versa. The addition of this element may have great importance after mitral replacement due to the fact that in some patients with severe heart diseases, the transmitral flow decreases making the opening pressure from the left auricle extremely low. These two factors provoke an unequal opening of both leaflets. This is to be avoided as a monovalve disfunction favors local remora and thrombosis and progressive risk of total thrombosis of the prosthesis is thereby created.

Each of the swivelling leaflets described above will, preferably, have a range of angle positions with respect to a plane perpendicular to the axis of the support ring between 40° in its closing position and 90° in its total opening position.

Other objects and advantages of the present invention will become apparent from the detailed description given hereinafter. It should be understood, however, that the detailed description and embodiments shown are given by way of illustration only, since various changes and modifications within the spirit and scope of the invention will become apparent to those skilled in the art.

In the drawing, wherein similar reference characters denote similar elements throughout the several views.

Figure 1:
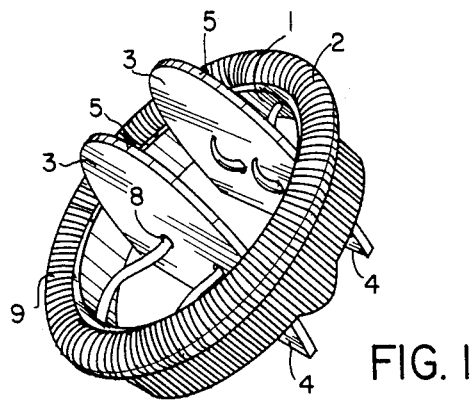
FIG. 1 is a perspective view of a mechanical cardiac prosthesis embodying the present invention.

Turning now in detail to the drawings and, in particular, FIG. 1 thereof, therein illustrated is a cardiac prosthesis of the mechanical type embodying the present invention which includes a rigid support ring 1, generally surrounded by a conventional suture Chord 2. Ring 1 constituting the valvular seat on which, in the closed position, two movable leaflets 3 are supported. The leaflets 3 may occupy two alternate end positions namely, a completely or total open position in which they are mutually parallel, and a completely or totally closed position, as shown in FIG. 2, in which both leaflets contact each other substantially diametrically along their straight central edges 4.

Leaflets 3 each comprise a rigid planar element having a semicircular shape, so that in the totally closed position, they contact support ring 1 only by the rim portion of their arcuate edges 5, while at the same time, they contact each other along their respective straight edges 4.

Figure 2:
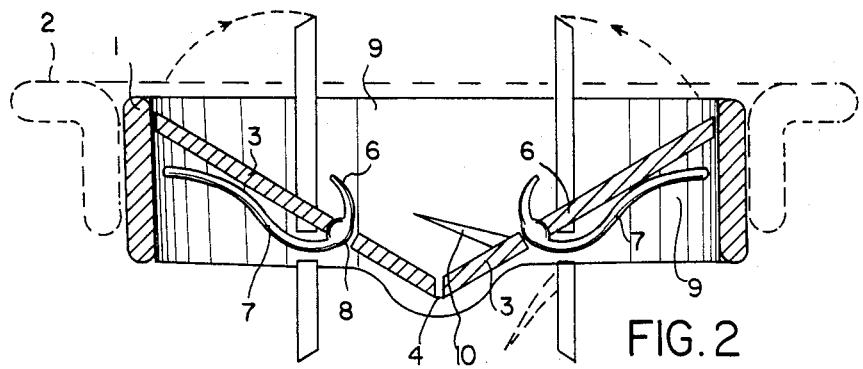
FIG. 2 is an enlarged, cross-sectional view of the prosthesis of FIG. 1 in its closed position.

Referring now to FIG. 2, leaflets 3 are each mounted on hook-shaped engagement end portions of oppositely-disposed paired pivot supports 7 via their orifices 8. As a result, they can move between the two aforementioned end positions, swivelling or pivoting with respect to corresponding virtual axes 6, which are parallel to diametrical edges 4 and lie within the zones containing the centers of curvature of both engagement end portions of the paired pivot supports 7. The two pivot supports 7 of each pair are parallel to one another and both pairs extend towards the central area of support ring 1, but such that the pairs are spaced apart from one another.

Pivot supports 7 are preferably made of wire rigidly embedded in the solid body of ring 1. It is preferable that the wire pivot supports 7 be of reduced gauge but of sufficient strength to indefinitely maintain their shape. As mentioned above, they pass through respective orifices 8 in valves 3. The location of those orifices and the distance with respect to the diametrical edges 4 of leaflets 3, permit the prostheses to afford different degrees of total opening in their central zone, thus allowing for different medical requirements.

With the wires constituting pivot supports 7 being thin, the inner surface 9 of the supporting ring is practically continuous, without interruptions. This minimizes the danger of coagula formations and the resultant aforementioned risk of thrombosis.

Figure 3:
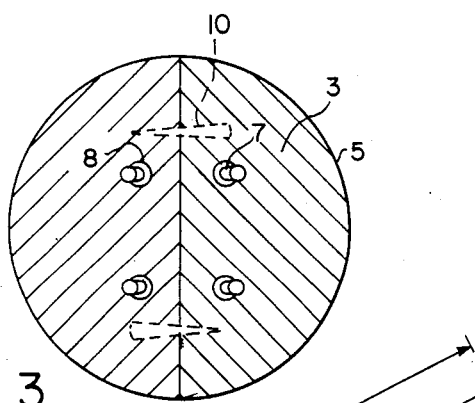
FIG. 3 is a plan view of the prosthesis in its totally closed position.
Figure 4:
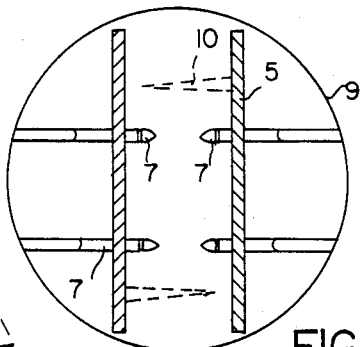
FIG. 4 is a plan view of the prosthesis in its totally opened position.

As shown in FIGS. 2–4, it is desirable in a further embodiment of the invention for at least one of the leaflets to be provided with a thin oblique stem 10 fixed to and extending from the upper planar surface thereof, for the purpose of facilitating the simultaneous opening of both leaflets, especially in mitral position.

As can be seen best in FIGS. 2 and 4, the curved ends of pivot supports 7 may serve as limit stops for the opening of the leaflets. Alternatively, small stops in the form of projections from the inner surface of support ring 1 may be used without altering in any way the concept of the invention.

In addition, the engagement formations or configurations of the free ends of pivot supports 7 need not be circumferential arcs. However, it is essential that they have a concavity oriented as, e.g., illustrated in the figures, such that the virtual axis 6 should be in the zone of the various resulting centers of curvature, provided the parallel position illustrated is not exceeded and the disengagement of the leaflets is prevented.

Figure 5:
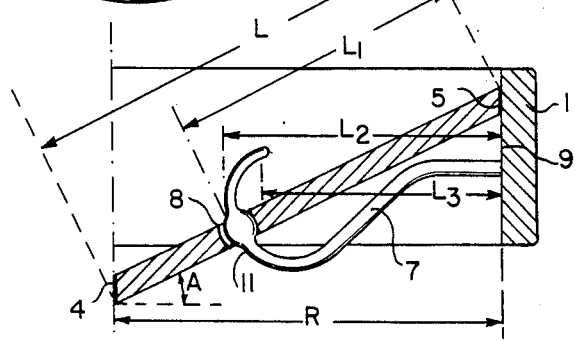
FIG. 5 is an enlarged, fragmentarily-illustrated view of the prosthesis, showing one of the valves in its closed position, and its pivot supports.

In FIG. 5, preferred dimensional parameters of the claimed invention are shown. Reference L denotes the radius of the circumferential arc forming the curved or arcuate edge 5 of each leaflets, measured from the center of the straight edge 4; $L_1$ denotes the distance between each orifice 8 and the center of the curved edge 5; $L_2$ indicates the distance between the greater projection of pivot support 7 and the inner surface 9 of support ring 1; $L_3$ indicates the distance between the tip of the free end or hook of pivot support 7 and inner surface 9; and R indicates the radius of curvature of support ring 1. The following relationships should be complied with:
  (a) L should be larger than R;
  (b) $L_1$ should be larger than $L_2$; and
  (c) $L_3$ should be smaller than $L_2$ and, consequently, smaller than $L_1$.

In FIG. 5 it is further possible to see that when leaflets 3 swivels from its closed to open position, its support by orifice 8 on the curved part of pivot support 7 is displaced downwardly and toward ring 1 until it reaches a vertical position, parallel with the other valve (see FIGS. 2 and 4) at which time the leaflets are in their maximum opening position. The leaflets may be optionally provided with stops in the form of small stems (not shown) fixed in ring 1.

As shown in FIG. 5, pivot supports 7 are provided with a thickened or bulbous segment 11 so that, in the valve closed position, segments 11 almost completely occlude orifices 8 of the valves. This detail is intended to limit the passage of blood which may regurgitate during valvular closure. Further, these localized enlargements of pivot supports 7 and the movement of leaflets 3 relative thereto act as a true protective mechanism by assuring permeability and permanent opening of orifices 8, thus preventing fibrin deposits or small clots. In fact, while life and cardiac functions exist, valvular closure is always originated by a high pressure mechanism; approximately 120 mm Hg for mitral closure and 80 mm Hg for aortic closure. At this time of cardiac cycle, orifices 8 of leaflets are almost completely occupied and thus closed off by bulbous segments 11. By contrast, opening pressure may be at a minimum, especially for mitral opening which should open with a pressure in the left atrium of 2 mm Hg. At this time in the cardiac cycle orifices 8 of the leaflets have swivelled toward the thinner segments of pivot supports 7.

While only several embodiments have been shown and described, it is obvious that many changes and modifications may be made without departing from the spirit and scope of the invention.

What is claimed is:

1. A mechanical-type, bivalve cardiac valvular prosthesis comprising:
  a support ring defining a central opening passing therethrough;
  a pair of relatively rigid leaflets disposed generally within said central opening, each of said leaflets having a diametrical straight edge and a curved edge; and
  means for pivotably supporting said pair of leaflets on said support ring to permit said leaflets to move between an open position, in which said leaflets are disposed generally parallel to the longitudinal axis of said support ring so that said central opening is substantially open and divided by said leaflets into two semi-circular areas disposed on either side of a generally rectangular central area, and a closed position, in which said opening is substantially blocked by said leaflets contacting each other substantially diametrically along their straight central edges, and contacting said support ring only along their curved edges, said means comprising a pair of spaced apart parallel pivot suports for each of said leaflets, said pivot supports each being rigidly joined at one end to said ring, and each having an opposite, generally semicircular hook-shaped, free end on which the leaflet associated therewith is mounted in a free floating manner so that said leaflets are freely and independently pivotable about a virtual axis parallel to said diametrical straight edges thereof and passing through the zone of the center of curvature of said hook-shaped ends of said pivot supports.

2. The prosthesis of claim 1, wherein said leaflets are planar and each has a generally semicircular configuration.

3. The prosthesis of claim 1, wherein said virtual axes are spaced apart at a distance equivalent to about one-third of the diameter of said support ring.

4. The prosthesis of claim 1, wherein said pivot supports are made of wire.

5. The prosthesis of claim 1, wherein each pair of pivot supports are joined to opposite regions of said support ring and project inwardly therefrom toward the center of said ring, but spaced apart from one another to define a central free zone which determines the mutual separation between the leaflets in their total opening position and wherein said leaflets in said totally open position form an angle of up to 90° with respect to a plane passing through the virtual axes.

6. The prosthesis of claim 1, wherein the distance between the center points of said arcuate edge and said straight edge of said leaflets is greater than the inner radius of said support ring.

7. The prosthesis of claim 1, wherein each of said leaflets has a pair of orifices formed therethrough which said free ends of said pivot supports pass, and wherein said orifices are located at a distance from the diametrical straight edge of the leaflets associated therewith which is less than half the distance between the central points of said straight edge and said arcuate edges of said associated leaflets.

8. The prosthesis of claim 7, wherein said hook-shaped end portions of said pivot supports have tips which are located at a distance from the inner surface of said support ring, at the point at which said one end of the corresponding pivot support is joined thereto, which is less than the distance between the corresponding orifice of the leaflets and the central point of the arcuate edge thereof.

9. The prosthesis of claim 7, wherein in the total closed position, said leaflets form an angle of about 40° with respect to a plane passing through the virtual axes.

10. The prosthesis of claim 1, wherein said pivot supports for each of said leaflets oppose each other.

11. The prosthesis of claim 1, wherein a stem is rigidly affixed to at least one of said leaflets in order to aid in simultaneous opening of said leaflets.

12. The prosthesis of claim 1, wherein each pivot support passes through an associated orifice in one of said leaflets, and different degrees of opening of said central opening may be provided, as medically required, by varying the position of said orifices on said leaflets.

13. The prosthesis of claim 12, wherein each support includes a bulbous segment generally disposed within said associated orifice.

* * * * *